United States Patent [19]
Kohn et al.

[11] Patent Number: 5,619,135
[45] Date of Patent: Apr. 8, 1997

[54] STEEL CHARACTERISTICS MEASUREMENT SYSTEM USING BARKHAUSEN JUMP SUM RATE AND MAGNETIC FIELD INTENSITY AND METHOD OF USING SAME

[75] Inventors: Gabriel Kohn, Omer, Israel; George Hicho, Derwood; Lydon Swartzendruber, New Carrollton, both of Md.

[73] Assignee: American Iron and Steel Institute, Washington, D.C.

[21] Appl. No.: 503,263

[22] Filed: Jul. 17, 1995

[51] Int. Cl.$^6$ .............. G01B 7/24; G01N 27/72; G01R 33/00
[52] U.S. Cl. .............. 324/239; 324/209; 324/262; 364/481; 73/779
[58] Field of Search .............. 324/209, 228, 324/239, 243, 262; 73/587, 779, 801; 364/508, 481

[56] References Cited

U.S. PATENT DOCUMENTS

| | | |
|---|---|---|
| 3,427,872 | 2/1969 | Leep et al. . |
| 3,783,370 | 11/1974 | Birdwell et al. .......... 324/209 |
| 4,481,470 | 11/1984 | Wallace . |
| 4,599,563 | 7/1986 | Tiitto et al. . |
| 4,634,976 | 1/1987 | Tiitto . |
| 4,689,558 | 8/1987 | Ruuskanen et al. . |
| 4,881,030 | 11/1989 | Stuecker et al. . |
| 4,977,373 | 12/1990 | Tiitto . |
| 5,313,405 | 5/1994 | Jiles et al. .............. 324/209 |

OTHER PUBLICATIONS

"Measuring Technology in Continuous Annealing," K. Kurita, The 88–89th Nishiyama Memorial Seminars, ed. by ISIJ, Tokyo (1983). 167, in Japanese version.

"Detection of Fabrication Stresses by the Barkhausen Noise Method," L.P. Karjalainen, et al., Effects of fabrication related stresses, Sep. 1985.

"Nondestructive Evaluation of Ferromagnetic Materials by a Magnetometer Like Experimental Arrangement," B.Z. Kaplan, et al., Journal of Nondestructive Evaluation, vol. 6, No. 2, 1987.

*Primary Examiner*—Walter E. Snow
*Attorney, Agent, or Firm*—Fitzpatrick, Cella, Harper & Scinto

[57] ABSTRACT

A steel hardness measurement system and method of using same are provided for measuring at least one mechanical or magnetic characteristic of a ferromagnetic sample as a function of at least one magnetic characteristic of the sample. A magnetic field generator subjects the sample to a variable external magnetic field. The magnetic field intensity of the magnetic field generated by the magnetic field generating means is measured and a signal sensor is provided for measuring Barkhausen signals from the sample when the sample is subjected to the external magnetic field. A signal processing unit calculates a jump sum rate first moment as a function of the Barkhausen signals measured by the signal sensor and the magnetic field intensity, and for determining the at least one mechanical or magnetic characteristic as a function of the jump sum rate first moment.

19 Claims, 7 Drawing Sheets

STEEL CHARACTERISTICS MEASUREMENT SYSTEM USING BARKHAUSEN JUMP SUM RATE AND MAGNETIC FIELD INTENSITY AND METHOD OF USING SAME

This invention was made with Government support under Contract No. DE-FC07-93ID13205 awarded by the Department of Energy. The Government has certain rights in this invention.

BACKGROUND OF THE INVENTION

1. Field of the Invention

The present invention relates generally to an apparatus and method for estimating certain mechanical properties of a ferromagnetic sample, such as steel, and, more particularly, relates to an apparatus and method for estimating the hardness of a sample of ferromagnetic low-carbon sheet steel by measuring and analyzing the Barkhausen signals measured from the sample when subjected to a varying external magnetic field. Preferably, the measurement can be made either on-line or off-line.

2. Background and Objects of the Invention

Approximately 65 million tons of sheet steel per year are produced in the United States. One of the challenges to the steel making industry today is to improve the ability to produce large quantities of sheet steel having well-controlled and uniform mechanical properties with a minimum amount of scrap steel produced. It is estimated that if the rejection rate of sheet steel could be cut in half, a savings on scrap on the order of $100 million per year could be realized. Still further benefits would result from the increased production efficiency realized by the end users of the steel and by reductions in the amount of the time-consuming and costly testing of the mechanical characteristics of the steel to be shipped to the end users, which is presently required.

Various mechanical properties of steel, such as hardness, strength, ductility and strain-hardening exponent, are structure-sensitive, and therefore are directly related to the microstructure and composition of the steel. In other words, the microstructure and composition of the steel directly affects these mechanical properties. As a result, if the microstructure can be analyzed, then the mechanical properties of the steel can be predicted.

The microstructure, composition, and processing of the steel also control, to a large extent, the magnetic characteristics of ferritic or ferromagnetic steel. For example, magnetic properties of these steels that are sensitive to microstructure include initial permeability, maximum permeability, coercive force, remanance, and the Barkhausen effect. Thus, if any of these magnetic characteristics of the steel can be measured reliably, then the microstructure of the steel can be predicted. In turn, the microstructure of the steel can then be used to predict the mechanical properties. Further, if sensitive measurements of the magnetic characteristics of the steel can be performed rapidly and on-line, then the mechanical properties can be predicted and the steel production process altered, as necessary, to customize the resultant characteristics of the steel.

Of the magnetic properties of steel mentioned above, the one which appears to the inventors to be most useful for predicting the hardness of the steel, either when the steel is stationary or while it is moving during processing, is the Barkhausen effect. As discussed in detail below, the Barkhausen effect may generally be characterized as a series of abrupt changes or jumps in the magnetization of a ferrous material (characterized by Barkhausen signals) when a magnetizing field applied to the material is gradually altered. The Barkhausen measurements discussed herein can also be combined with other on-line measurements, such as, for example, grain size, to improve predictive capabilities.

Although the Barkhausen effect in and of itself is a known scientific phenomenon, its use in the apparatus and methods of the particular preferred embodiments disclosed herein is novel and unobvious. For example, U.S. Pat. No. 4,599,563 to Tiitto et al. appears to disclose the general concept of sensing the Barkhausen signals generated within a steel specimen in a plurality of directions to determine anisotropic properties of the steel. Anisotropic properties are said to include hardness. (See, e.g., column 2, lines 15–27 and 47–52; and column 3, lines 3–15). However, the manner in which the Barkhausen signals are used by the Tiitto et al. '563 system differs substantially from that of the present invention. The particular features of the present apparatus and method are neither disclosed nor suggested by Tiitto et al. '563.

U.S. Pat. No. 4,481,470 to Wallace discloses a method for determining the amount of hardness in strain-hardened articles of tungsten-nickel-iron alloy by measuring the magnetic flux emanating from the article. The use of the Barkhausen effect is not disclosed.

Kurita, "Measuring Technology in Continuous Annealing", *Transactions ISIJ*, vol. 26, 1986, pp. 3–22, recognizes that the hardness of steel is closely related to the grain size of the steel. The hardness of rolled steel is measured by magnetizing the steel and measuring the leakage of the resulting magnetic field. Kurita relies on the premise that the leakage varies with the grain size of the steel and may therefore be used to determine hardness. Kurita also discloses magnetizing a strip of steel and measuring the residual magnetism. The hardness of the steel is determined as a function of the residual magnetism. Use of the Barkhausen effect is not disclosed by Kurita.

Karjalainen et al., "Detection of Fabrication Stresses by the Barkhausen Noise Method", *Effects of Fabrication Related Stresses*, September, 1985, pp. 149–161, and Kaplan et al., "Nondestructive Evaluation of Ferromagnetic Materials by a 'Magnetometer Like' Experimental Arrangement", *Journal of Nondestructive Evaluation*, Vol. 6, No. 2, 1987, pp. 73–79, and U.S. Pat. Nos. 3,427,872 to Leep, 4,689,558 to Ruuskanen et al., 4,977,373 to Tiitto and 4,881,030 to Stuecker et al., each disclose systems for measuring Barkhausen signals to determine residual stress or fatigue limit in ferromagnetic materials, such as steel. Measuring hardness as a function of the Barkhausen signals is not disclosed.

Lastly, U.S. Pat. No. 4,634,976 to Tiitto discloses a particular sensor configuration employing the Barkhausen effect for detecting stresses and structural defects in metal. The particular features of the present apparatus and method, however, are neither disclosed nor suggested by Tiitto '976.

Accordingly, it is an object of the present invention to provide a steel hardness measurement system and method of using same by which the Barkhausen signals in a specimen of steel, such as low carbon, rolled sheet steel, are measured as a function of one or more of a variety of parameters, to give an indication of the hardness of the steel.

It is a further object of the present invention to provide a system and method for measuring the hardness of the steel by measuring the Barkhausen signal emission rate as a function of the magnetic field intensity H.

It is a further object of the present invention to provide a system and method for measuring the hardness of the steel by measuring the Barkhausen signal emission rate as a function of the magnetic field intensity H.

It is a still further object of the present invention to provide a system and method capable of measuring the Barkhausen signal in a steel sample that is subjected to various stress samples.

It is yet a further object of the present invention to provide a system and method for measuring the Barkhausen signals in either a stationary or moving sample of steel.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

SUMMARY OF THE INVENTION

To achieve the foregoing objects, and in accordance with the presently preferred embodiments of the present invention, there is provided a steel hardness measurement system and method of using same comprising an apparatus and method for measuring at least one mechanical or magnetic characteristic of a ferromagnetic sample as a function of at least one magnetic characteristic of the sample, the apparatus and method comprising a magnetic field generator for subjecting the sample to a variable external magnetic field. The magnetic field intensity of the magnetic field generated by the magnetic field generating means is measured and a signal sensor is provided for measuring Barkhausen signals from the sample when the sample is subjected to the external magnetic field. A signal processing unit calculates a jump sum rate first moment as a function of the Barkhausen signals detected by the signal sensor and the magnetic field intensity, and determines the at least one mechanical or magnetic characteristic as a function of the jump sum rate first moment. The signal processing unit may incorporate a knowledge base to provide, for example, for relating mechanical and magnetic properties in various grades of steel.

BRIEF DESCRIPTION OF THE DRAWINGS

The following detailed description of the preferred embodiments can be better understood if reference is made to the accompanying drawings in which.

DESCRIPTION OF THE PREFERRED EMBODIMENTS

Figure 1:
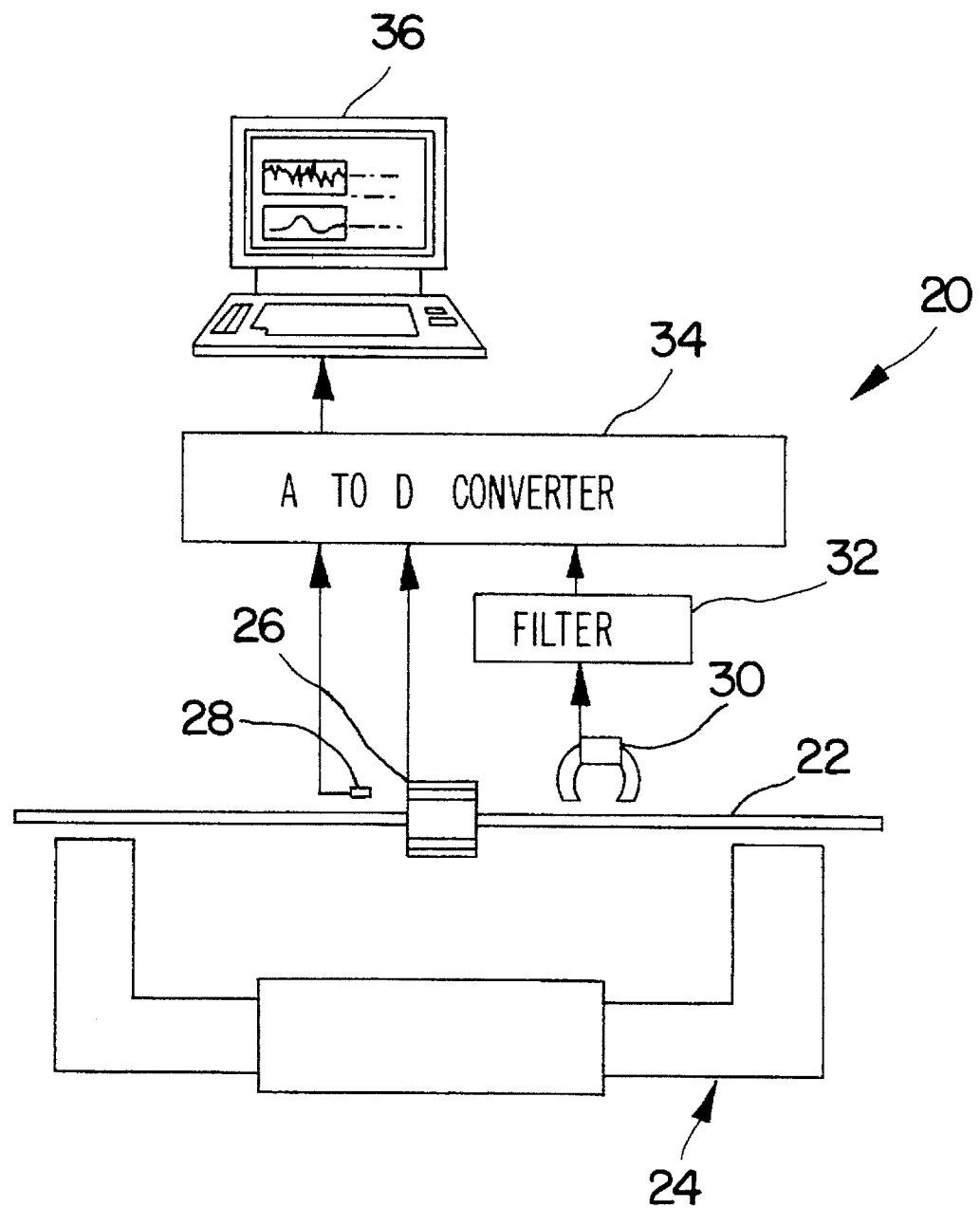
FIG. 1 is a general system block diagram of a preferred embodiment of the apparatus and method of the present invention.

Reference will now be made in detail to the present preferred embodiments of the invention, examples of which are illustrated in the accompanying drawings and described herein. Wherever possible, the same reference numbers will be used throughout the drawings to refer to the same or like parts.

The Barkhausen effect will now be explained in more detail, with particular emphasis on how it is used by the apparatus and method of the present invention. The Barkhausen effect is defined by Van Nostrands's *Scientific Encyclopedia*, Seventh Edition (1989), as a series of minute "jumps" in the magnetization of iron or other ferromagnetic substance as the magnetizing force is continuously increased or decreased. The jumps are due to the variations in size and orientation of small regions of the ferromagnetic material. More specifically, ferromagnetic substances, at the sub-atomic level, include a series of magnetic domains, each of which has a particular magnetization. The magnetizations, or moments, of the respective domains may be oriented in any direction and are separated by domain walls. Because the magnetizations may vary in direction from domain to domain, the magnetizations may change direction abruptly across a domain wall separating adjacent domains.

When an external magnetic field is applied to the ferromagnetic material, the magnetizations of the magnetic domains will seek to become aligned in the direction of the magnetic field, in accordance with known magnetic theory. To affect the alignment of the magnetizations of the magnetic domains, the domain walls will attempt to move or jump (i.e., the "jumps" referred to by Van Nostrand). The domain walls, however, may be pinned by impurities (such as C atoms, N atoms or fine precipitates) or physical imperfections within the micro structure of the ferromagnetic material.

The effects of the application of a varying external magnetic field on a ferromagnetic material, such as steel, are commonly expressed as a hysteresis loop, not shown, which is a plot of the magnetic flux density B of the substance as a function of the applied magnetic field intensity H. As the magnetic field intensity H increases, the magnetic flux density B increases as well, but lags the intensity H. At the saturation point, the magnetic flux density B stops increasing, despite the still-increasing magnetic field intensity H. When the magnetic field intensity H is decreased, the magnetic flux density B decreases, but again lags the magnetic field intensity H until a second saturation point is reached.

By applying a hysteresis loop to the ferromagnetic material, and measuring how the magnetic flux density B varies with the magnetic field intensity H the Barkhausen signals, representing how the domain walls move or jump from one pinning site to another when in the presence of an external magnetic field, may be detected. As a result of the Barkhausen signals, specifically detected as the change in magnetic flux in the substance over time, mechanical properties of the microstructure of the substance, such as hardness, may be examined, as discussed in detail below.

Referring to FIG. 1, there is illustrated a presently preferred embodiment of the steel hardness measurement system 20 of the present invention. The system 20 measures the magnetic properties of a ferromagnetic sample 22. Steel sample 22 is preferably rolled sheet steel, i.e., steel having a thickness of approximately 2 mm or less. Sample 22 also preferably contains less than approximately 0.1 wt.-% carbon, such as ultra-low carbon (ULC), low-carbon (LC) or high-strength-low-alloy (HSLA) steel. It should be understood, however, that the sample 22 itself does not comprise a necessary element of the present invention. The relative size of system 20 and the components thereof, discussed below, are not critical to the operation of the apparatus and method of the present invention and may be varied, for example, as a function of the size of sample 22.

The system 20 preferably comprises an energizing yoke 24, a Hall probe 28 and a signal sensor 30. Optionally, a pickup coil 26 may also be provided. A filter 32 is provided and receives a signal output from the signal sensor 30. Filter 32 in turn provides an output signal to an analog-to-digital (A/D) converter 34, which also receives signals output from the pickup coil 26 (if provided) and the Hall probe 28. The A/D converter 34 outputs a signal to a signal processing unit 36, or to other appropriate apparatus for signal processing, as will be understood by those of ordinary skill in the art. Signal processing unit 36 may, in turn, be connected to a monitor, printer or other output device (only a monitor is shown) for displaying, printing or otherwise outputting information.

Energizing yoke 24 may be of any of a variety of suitable known constructions for applying an external, variable magnetic field to sample 22. That is, as shown in FIG. 1, energizing yoke 24 is positioned proximate to the sample 22 and applies a varying external magnetic field to the sample 22 so as to sweep the sample 22 through a hysteresis loop. More particularly, energizing yoke 24 applies a variable magnetic field to sample 22, the field being gradually increased and decreased in turn. If it is assumed that the sample 22 is a ferromagnetic material, such as steel, the magnetic flux density B exhibited by the sample 22 will generally follow the hysteresis pattern described above as the intensity of the applied external magnetic field is gradually increased and decreased by the energizing yoke 24. The variation of the magnetic field applied by energizing yoke 24 may be controlled either manually by the operator, or automatically, such as by software or the like, or by other means, as will be apparent to those of ordinary skill in the art.

Pickup coil 26 may optionally be provided to measure ordinary magnetic properties of sample 22, such as, for example, the magnetic flux density B of the sample, the coercive force of the sample, the magnetic susceptibility of the sample or the saturation magnetization of the sample. While these properties are not used directly by the apparatus and method of the present invention to determine the hardness of the sample 22, the properties nevertheless may be useful to the operator of the apparatus for other applications. The particular configuration of pickup coil 26 is not critical to the present invention and may be altered in accordance with the signals to be measured and the particular applications desired by the operator, as will be apparent to those skilled in the art.

Hall probe 28 is provided to measure the tangential magnetic field intensity H at the surface of the sample 22. As a result, the location of the zero tangential field point may be determined. This is particularly useful for calibration purposes. For example, stray magnetic fields emanating from the sample 22 may result in a shift of the output of the Hall probe 28, which could then be corrected. Hall probe 28 may be of any of a variety of known constructions.

Signal sensor 30 may comprise any of a variety of known coil sensor types for measuring the Barkhausen signal, i.e., the change in the magnetic flux in sample 22 over time, $d\Phi/dt$. Examples of suitable Barkhausen signal sensors include, for example, encircling coils, surface pancake coils, ferrite core surface coils, and the like, as will be apparent to those of ordinary skill in the art. The ability to select any of such a variety of acceptable Barkhausen signal sensors depending, for example, on the particular application and on commercial factors such as cost and availability, results from the present inventors' determination that for several low carbon steels with uniform cross section, the shape of the Barkhausen signal, $d\Phi/dt$, is nearly independent of the sensor geometry. That is, the peak output of the Barkhausen signal, $d\Phi/dt$, occurs at substantially the same value of magnetic field intensity H for each sensor configuration. Accordingly, the present invention provides advantageous simplicity and flexibility for its operators.

As will be described in more detail below, the apparatus and method of the present invention are effective both when sample 22 is stationary, and when sample 22 is moving, i.e., while the sample 22 is being processed (The particular means and speed by which sample 22 is moved or advanced during the rolling process are not critical to the operation of the present invention and will not be discussed in detail). In a preferred embodiment, for on-line measurements, that is, measurements made while the sample 22 is moving, signal sensor 30 preferably comprises a surface coil. The use of a surface coil as the signal sensor 30 provides the advantage that a coil encircling the sample 22 is not needed.

The signal sensor 30 also may comprise an array of sensors (not shown) for measuring the Barkhausen signal, $d\Phi/dt$, in the sample 22. The particular configuration and location of the array of sensors are not critical to the performance of the present invention, and may readily be determined and optimized by one of ordinary skill in the art. For example, the array of sensors may be provided on only one side of sample 22, or may be provided both over and under the sample 22 to reduce the effect of variations in the distance between the sample 22 and the sensors comprising the sensor array. In such a case, if the sheet moves closer to the top array of sensors, the signals output from the top sensors will increase, while the signal from the sensors positioned below sample 22 will decrease. As a result, the total signal output by the array of sensors will remain substantially constant. Further, as described in more detail below, because the sample hardness measurement determination of the present invention depends primarily on the value of the magnetic field intensity H at which the peak Barkhausen signal, $d\Phi/dt$, is measured, rather on the value of the peak value, $d\Phi/dt$, itself, the dependence on variations in the distance between the sample 22 and signal sensor 30 is reduced.

Filter 32 filters the Barkhausen signal, $d\Phi/dt$, measured by the signal sensor 30. Filter 32 comprises, for example, a band pass filter which passes signals of a predetermined frequency band, such as between 1 KHz and 100 KHz. Filter 32 thus comprises a means by which extraneous or transient signals measured by signal sensor 30 may be excluded from signal processing unit 36. Filter 32 also serves to exclude from the signal processing unit 36 the harmonics of the driving frequency at which the energizing yoke 24 is driven.

A/D converter 34 may be any of a number of known configurations, as will be apparent to those of ordinary skill in the art. A/D converter 34 receives as input signals the analog signals output by pickup coil 26, Hall probe 28 and filter 32 and converts the input signals into digital form. The digital signals are then output by A/D converter 34 to signal processing unit 36.

The particular configuration of signal processing unit 36 is not critical to the practice of the present invention and may comprise any of a variety of known commercially available configurations, as will be apparent to those of ordinary skill in the art. Signal processing unit 36 preferably comprises a programmable processor., such as a Model 486 processor commercially available from Intel Corporation or the like, capable of performing signal processing.

The operation of the presently preferred embodiments of the apparatus and method of the present invention will now be described.

Sample 22, which may comprise, for example, either a sample of sheet steel that already has been rolled (i.e., a stationary sample) or may comprise moving sheet steel that is in the process of being rolled, is subjected to the variable, external magnetic field created by energizing yoke 24. The magnetic field intensity H is gradually increased and decreased, so as to subject the sample 22 to a hysteresis loop. Because it is made of a ferromagnetic material such as steel, sample 22 will respond to the externally applied magnetic field at the microscopic level. More particularly, as described above, the domain walls of the sample 22 will jump in response to the magnetic field applied by the energizing yoke 24 in an attempt to align the magnetizations of the magnetic domains of sample 22 with the external magnetic field.

The jumps of the domain walls of sample 22 are measured as changes in the magnetic flux over time, $d\Phi/dt$, by the signal sensor 30. The Barkhausen signal, $d\Phi/dt$, output by the signal sensor 30 is filtered by filter 32 and is digitized by A/D converter 34. The digitized Barkhausen signal is then passed to signal processing unit 36. Signal processing unit 36 also receives a signal output from the Hall probe 28 representing the magnetic field intensity H. This signal is also first digitized by A/D converter 34. Finally, signal processing unit 36 may also receive a signal, or signals, from pickup coil 26 representing ordinary magnetic properties of sample 22, should pickup coil 26 be provided. These signals, if any, are also first digitized by A/D converter 34.

In the signal processing unit 36, the Barkhausen signal, $d\Phi/dt$, measured by the signal sensor 30, is analyzed as a function of the magnetic field intensity signal H measured by the Hall probe 28. First, signal processing unit 36 performs a discrimination function to determine whether or not the signal measured by the signal sensor 30 is a valid signal, i.e., a signal caused by the Barkhausen effect, or is due to unwanted noise in the system. For example, if the magnetic field intensity H of the magnetic field applied by the energizing yoke 24 is less than zero, then one would not expect any Barkhausen signals to be generated. Any signals measured by the signal sensor 30 at magnetic field intensities where no Barkhausen effect is expected are discarded as noise.

Further, the height of the jumps in the Barkhausen signal, $d\Phi/dt$, measured by the signal sensor 30 are analyzed by the signal processing unit 36. A threshold level may be determined by the signal processing unit 36 in accordance the level of noise measured by signal sensor 30 when no Barkhausen effect is present. Signals output by signal sensor 30 to signal processing unit 36 that have a value exceeding such threshold are deemed to be valid and are subject to further processing, as described below. Signals output by signal sensor 30 to signal processing unit 36 that have a value less than the threshold are deemed to be invalid and are discarded as noise.

Next, the signal processing unit 36 sums the Barkhausen signals, $d\Phi/dt$, over a certain time period, $\Delta t$, to yield a jump sum. A jump sum rate (JSR) signal, which is a rate of the emission of the Barkhausen signal, may then be determined by dividing the jump sum signal by the time interval, $\Delta t$.

If the jump sum rate signal, JSR, is plotted as a function of the magnetic field intensity H measured by the Hall probe 28 and passed to the signal processing unit 36, a relationship between the JSR signal and certain mechanical properties of the sample 22 begins to emerge. Specifically, the inventors of the present invention have discovered that the center of gravity of the jump sum rate/magnetic field intensity plot is closely related to the hardness of sample 22. Accordingly, this point, known as the jump sum rate first moment (JSR first moment), is determined over time by signal processing unit 36. As the JSR first moment is calculated by signal processing unit 36, the calculated JSR first moment values may be compared against known values using a look-up table or the like to determine the hardness of the sample 22, as will be apparent to those of ordinary skill in the art. That is, the signal processing unit 36 may incorporate a knowledge base to provide, for example, for relating mechanical and magnetic properties in various grades of steel.

By determining the JSR first moment in order to predict the hardness of sample 22, the apparatus and method of the present invention minimize the effect of the width of each Barkhausen signal. This is advantageous because the width of the Barkhausen signals is greatly susceptible to variations in factors other than the hardness of the sample 22. For example, the width of the Barkhausen signals is a function of both the conductivity, $\sigma$, and permeability, $\mu$, of sample 22. Using the JSR first moment removes the dependence of the hardness determination on these factors.

Figure 2:
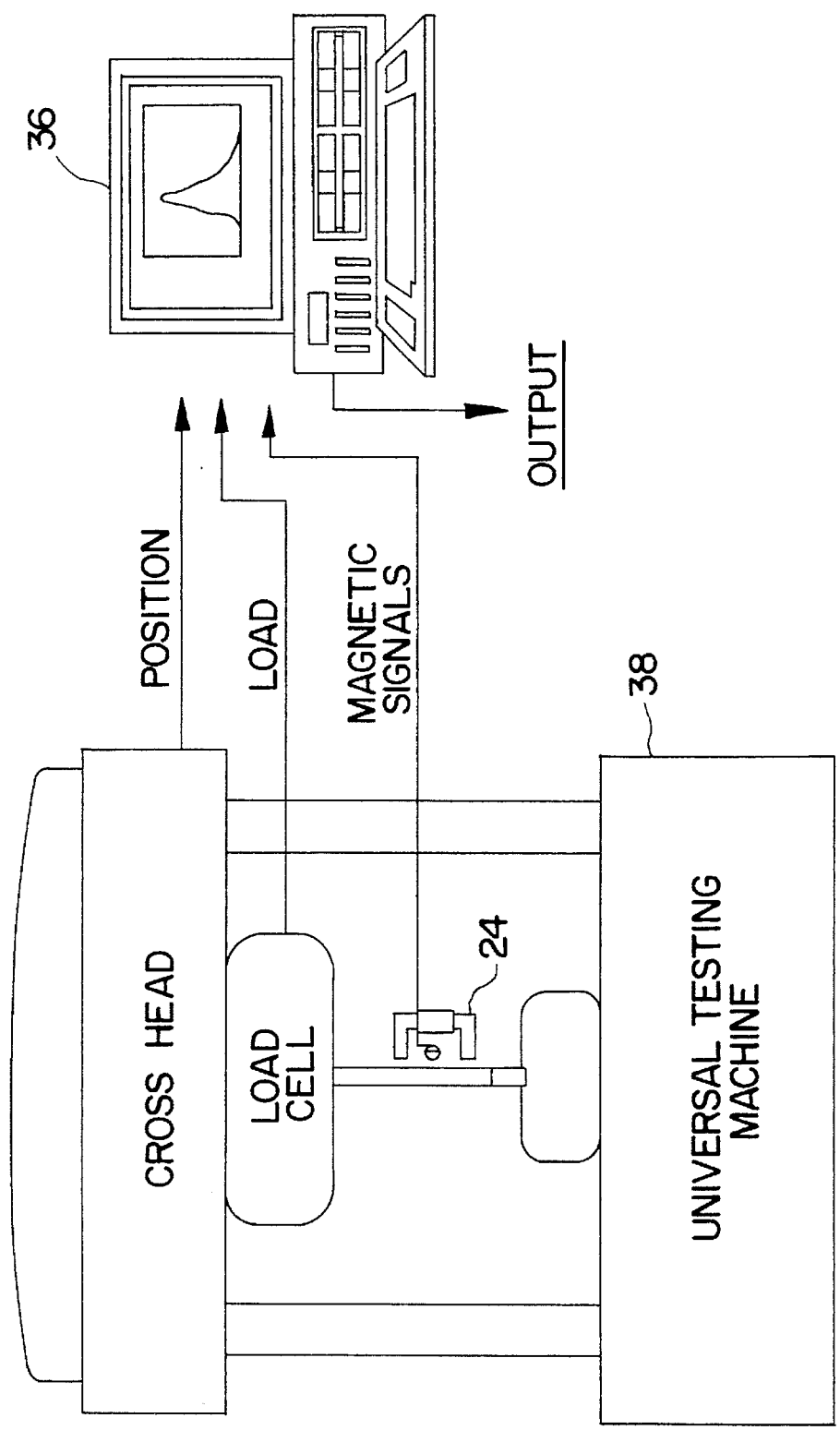
FIG. 2 is a system block diagram in which various components of the system of FIG. 1 are provided with a tensile testing apparatus.

The Barkhausen signal is known to be sensitive to stress. Thus, according to another preferred embodiment of the present invention shown in FIG. 2, there is provided a tensile testing apparatus 38 for applying a stress to the sample 22 as it is being analyzed. It is therefore possible to assess the effect of residual stress on the magnetic measurements made by system 20. This is particularly advantageous in an on-line environment, that is, one in which the sample 22 is being rolled, because of the various stress levels to which the sample 22 is exposed during the rolling operation at various points along the mill.

Tensile testing apparatus 38 may comprise, for example, a screw driven universal testing machine, or the like, of known construction, as will be understood by those of ordinary skill in the art. Apparatus 38 may be used to apply a continuous constant stress level to the sample 22, or may be varied to apply a continuously increasing or decreasing stress level.

Various tests of a prototype system 20 embodying the teachings of the present invention, used with and without tensile testing apparatus 38, have been performed by the inventors, the results from which are discussed generally below in connection with FIGS. 3 through 7. More particularly, tensile testing apparatus 38, when used, applied stress levels of, for example, 1, 3, 6 and 10 ksi (7, 21, 42 and 70 MPa), respectively, for each of a ULC steel sample, an LC steel sample, and a HSLA steel sample. In some cases, measurements were taken by the various components of system 20 while the tensile testing apparatus 38 applied a continuously increasing load to the samples 22, the stress level being increased at a rate of 0.1 mm/min. In other cases, the samples 22 were preloaded to one of the above stresses at a loading rate of 3.2 mm/min. and then held under constant stress by tensile testing apparatus 38 while the components of system 20 obtained the necessary measurements. This procedure was then repeated for the remaining stress levels. A thin foil of Permalloy was taped on the side of each sample 22 opposite the Hall probe 28 and the signal sensor 30. The signal measured by the Hall probe 28 from the Permalloy foil was used in the determination of the location of the zero tangential field point, as described above. Stray magnetic fields emanating from the sample 22 resulted in a shift in the reading of the Hall probe 28, which could thus be corrected.

Figure 3:
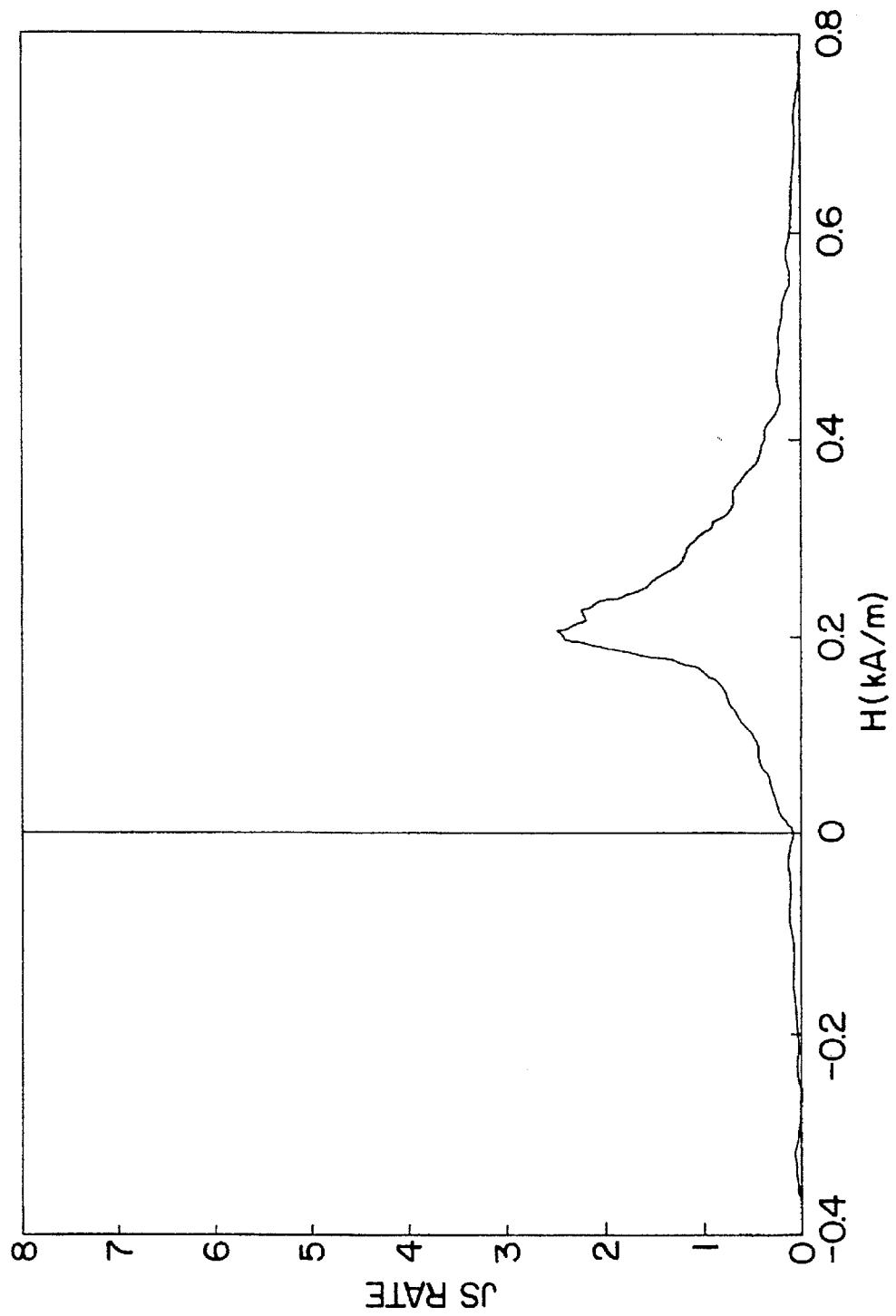
FIG. 3 is a plot of the Barkhausen signal emission rate as a function of the intensity of the tangential magnetic field applied to a sample of low-carbon steel, which illustrates various features of the apparatus and method of the present invention.
Figure 4:
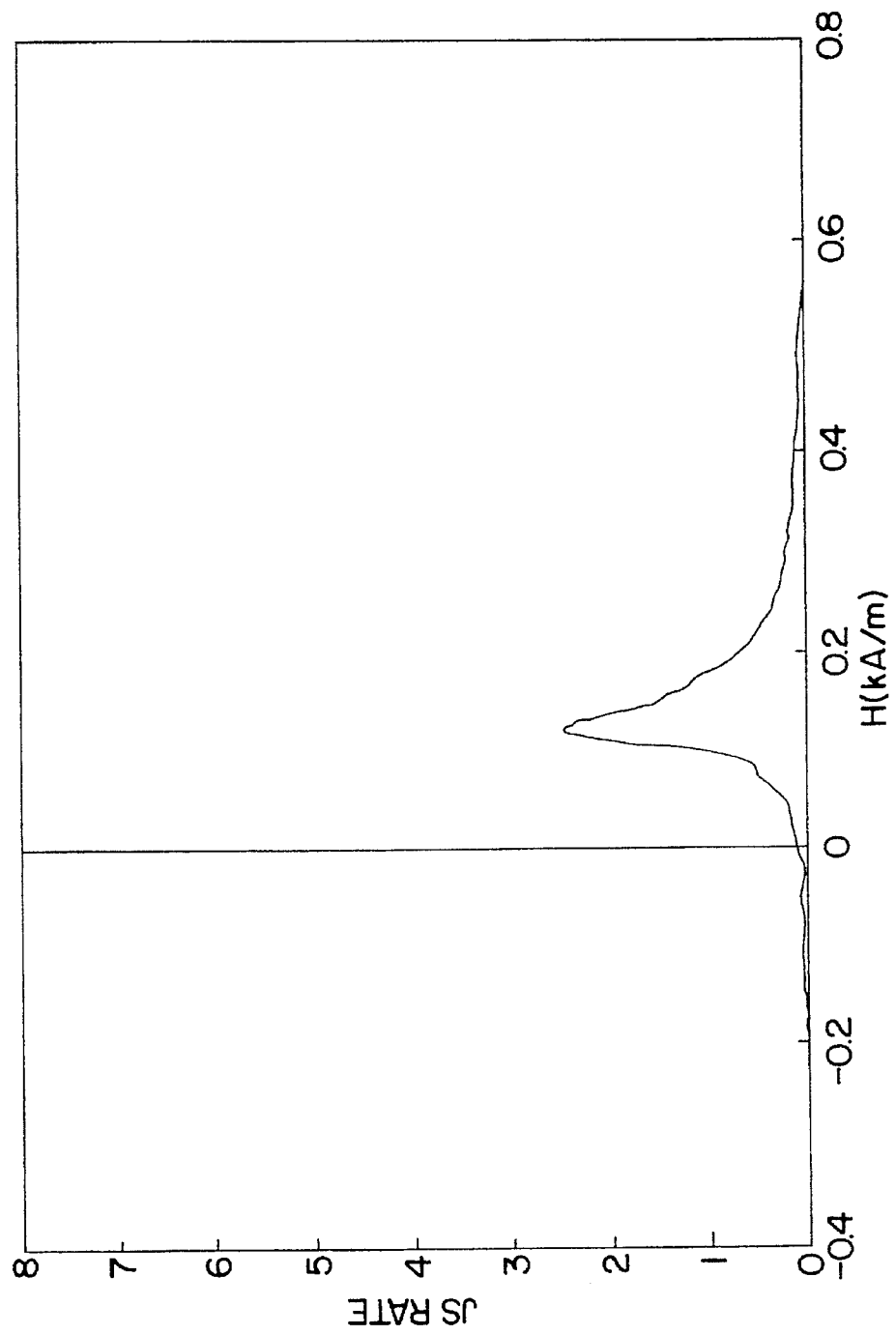
FIG. 4 is a plot of the Barkhausen signal emission rate as a function of the intensity of the tangential magnetic field applied to a sample of ultra low-carbon steel, which illustrates various features of the apparatus and method of the present invention.
Figure 5:
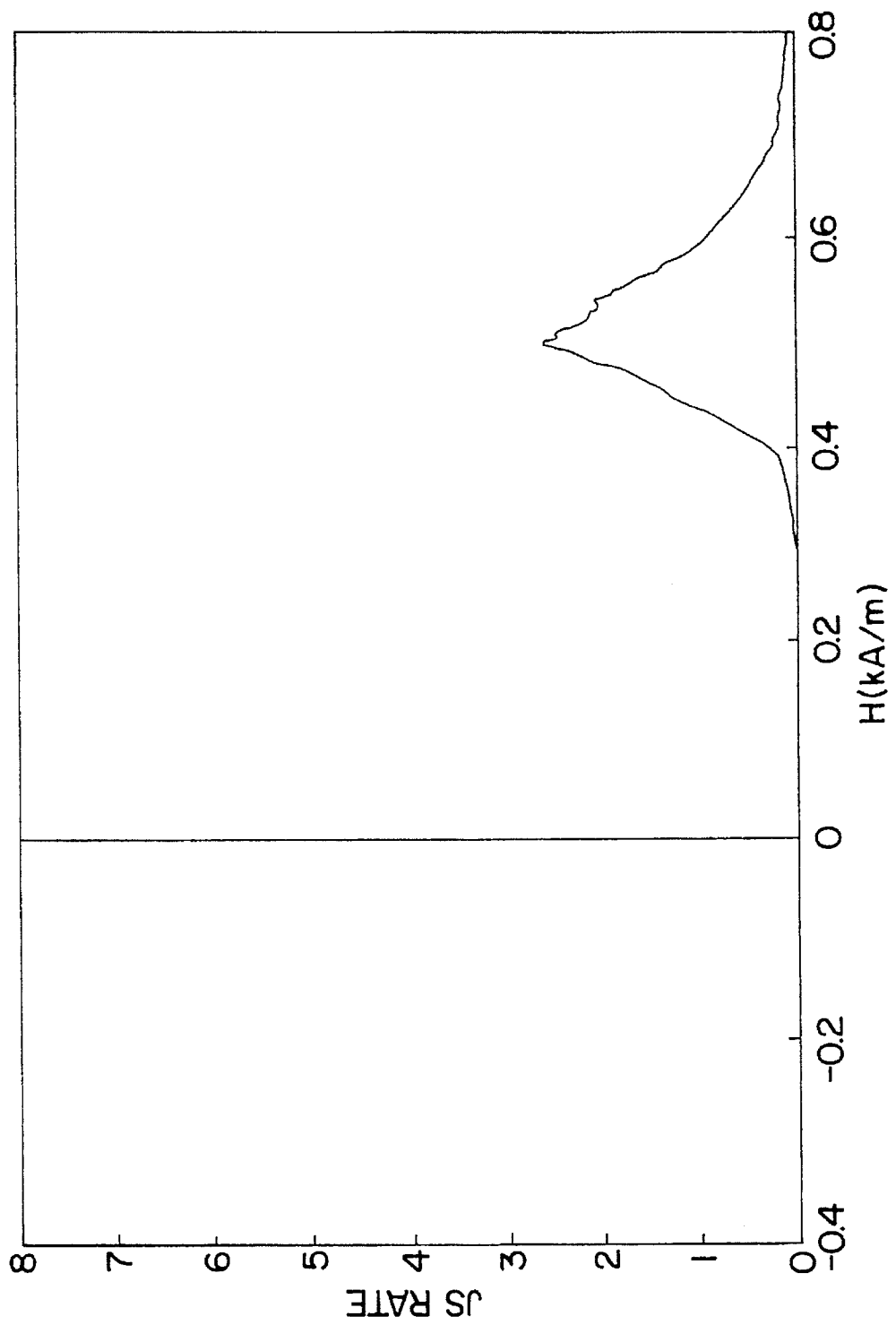
FIG. 5 is a plot of the Barkhausen signal emission rate as a function of the intensity of the tangential magnetic field applied to a sample of high-strength-low-alloy steel, which illustrates various features of the apparatus and method of the present invention.

Referring, for example, to FIG. 3, there is shown a plot of the Barkhausen signal emission rate, JSR, as a function of the intensity H of the tangential magnetic field applied to a sample 22 of low-carbon steel. Similarly, FIG. 4 shows a plot of the Barkhausen signal emission rate, JSR, as a function of the intensity H of the magnetic field applied to a sample 22 of ultra low-carbon steel. Finally, FIG. 5 shows a plot of the Barkhausen signal emission rate, JSR, as a function of the intensity H of the magnetic field applied to a sample 22 of HSLA steel. As can be seen from respective plots of FIGS. 3 through 5, the JSR curves are shifted as a function of the tangential magnetic field intensity H measured by Hall probe 28, for given types (e.g., carbon contents) of samples 22.

Figure 6:
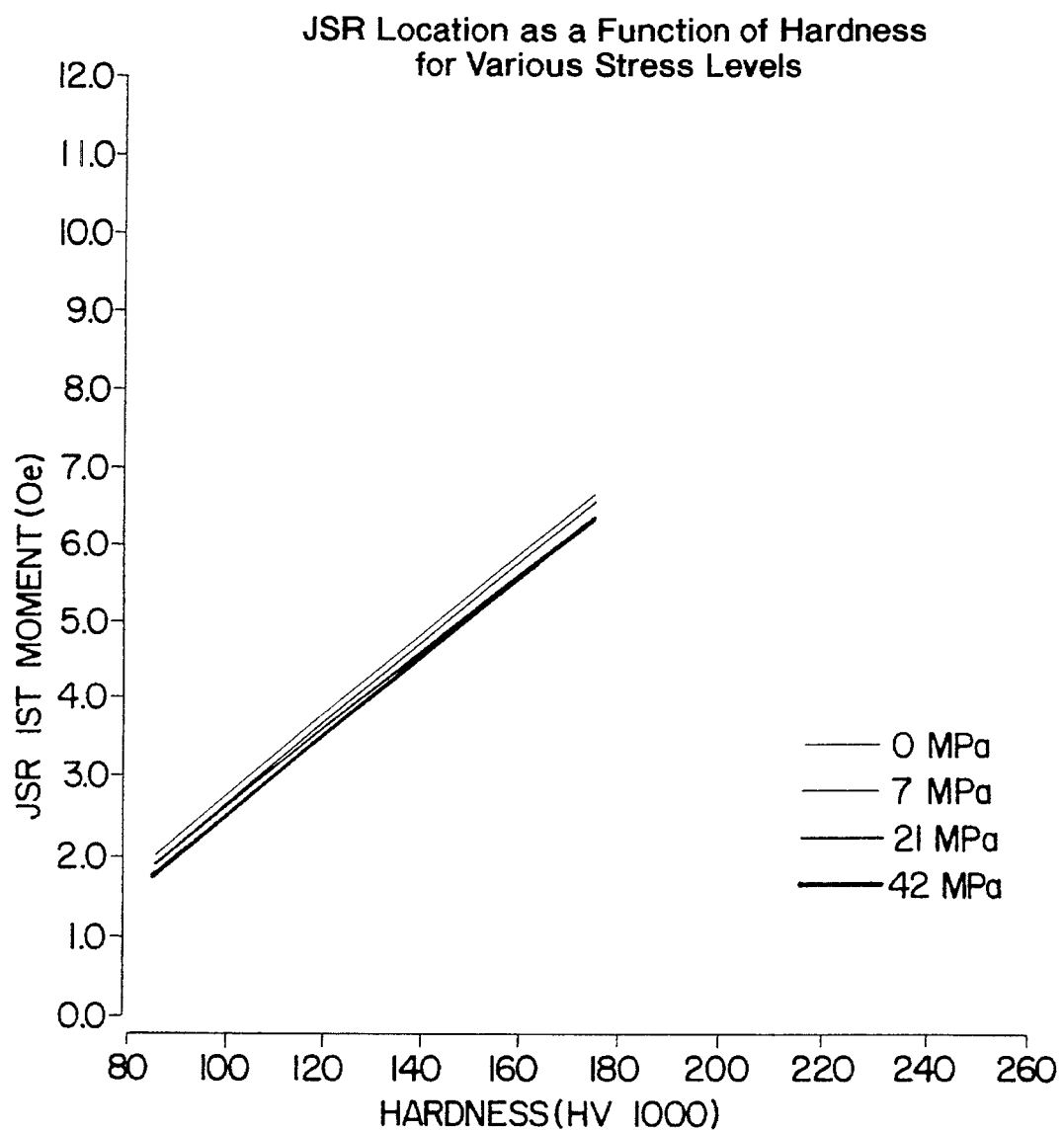
FIG. 6 is a plot of the jump sum rate (JSR) first moment of a sample as a function of the hardness of sample when the sample is subjected to various stress levels by the tensile testing apparatus illustrated in FIG. 2.
Figure 7:
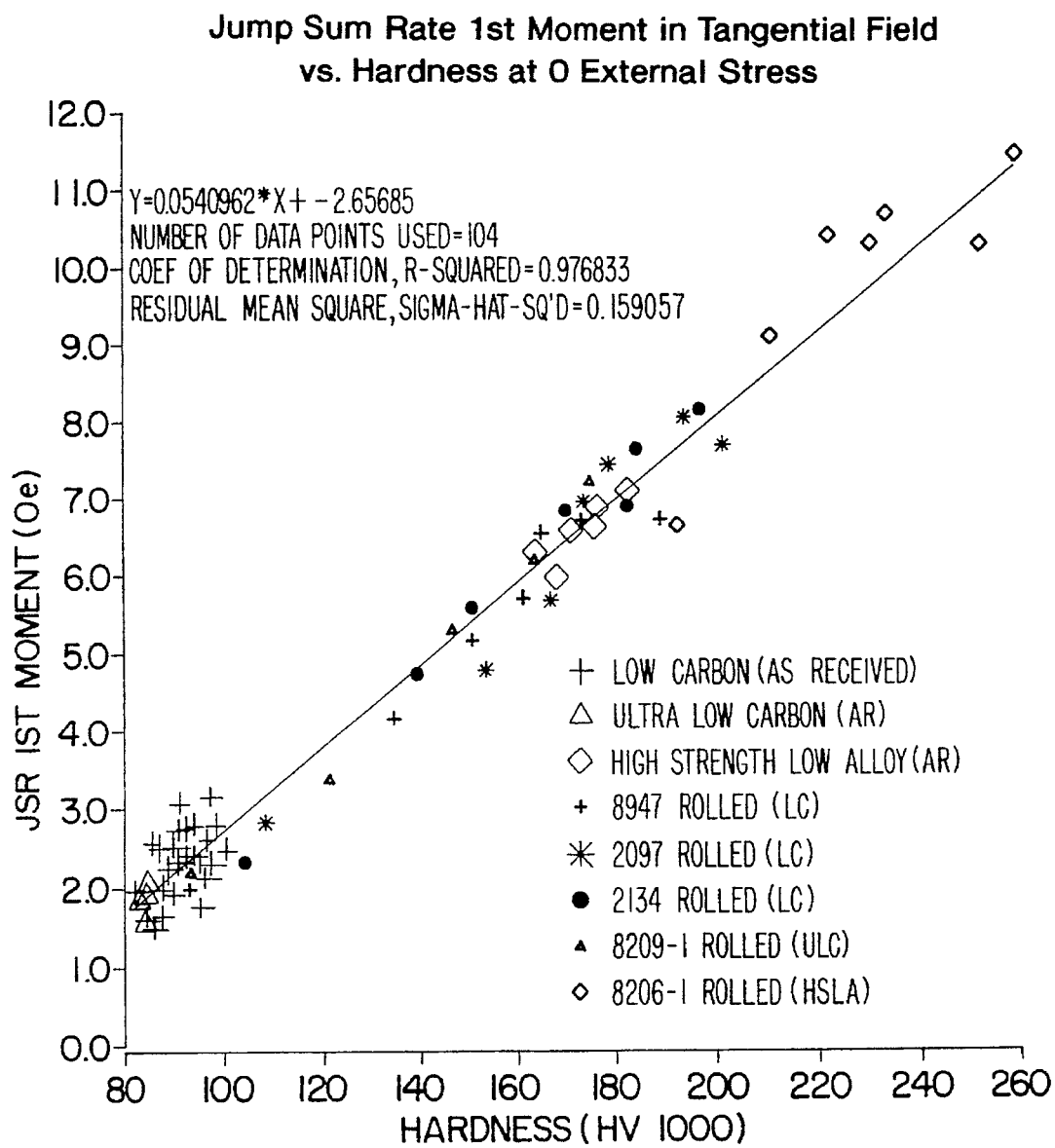
FIG. 7 is a plot of the JSR first moment of a sample as a function of the hardness of sample when no external stress is applied to the sample.

Referring now to FIG. 6, there is shown a plot of the JSR first moment of a sample 22 as a function of the hardness of sample 22 when sample 22 is subjected to various stress levels by tensile testing apparatus 38. FIG. 7 is a graph showing the JSR first moment as a function of the hardness of samples 22 of varying carbon content with no external stress being applied to sample 22 by tensile testing apparatus 38. As can be seen from FIGS. 6 and 7, there is a linear relationship between the JSR first moment and the hardness of the sample 22. Based on test results such as these, a data base in the form of a look-up table or the like, may be compiled for access by signal processing unit 36.

Signal processing unit 36 thus may provide a real-time indication to the operator of system 20, via any of various output means, such as a monitor, printer, or the like (again, only the monitor is shown), of the hardness of sample 22. With such information, the operator may make any adjustments in the rolling operation that may be necessary to produce the desired hardness of the sample 22 as it is being rolled. Alternatively, the hardness information may be provided to a feedback control loop by means of which various parameters may be adjusted or controlled as a function of the hardness of sample 22, or other mechanical or magnetic properties. For example, in a similar manner, the ordinary magnetic properties measured by the pickup coil 26 also may be processed by signal processing unit 36 and information of interest communicated to the operator or to a feedback loop.

As a still further example, artificial intelligence may be used, for example by signal processing unit 36, to make the optimum use of the mechanical or magnetic properties determined in accordance with the apparatus and method of the present invention.

While the present invention has been described with reference to what is presently considered to be the preferred embodiments, it is to be understood that the invention is not limited to the disclosed embodiments. To the contrary, the present invention is intended to cover various modifications and equivalent arrangements included within the spirit and scope of the appended claims.

For example, the inventors of the present invention have also determined that there is a linear correlation between the JSR first moment of a sample 22 of ferromagnetic material such as low-carbon steel, and the coercive field strength Hc of the sample, the yield strength, YS, of the sample, the ultimate strength, UTS, of the sample, and the flow strength of the sample.

The scope of the following claims is to be accorded the broadest interpretation so as to encompass all such modifications and equivalent structures and functions.

What is claimed is:

1. An apparatus for measuring at least one mechanical or magnetic characteristic of a ferromagnetic sample as a function of at least one magnetic characteristic of the sample, the apparatus comprising:

magnetic field generating means for subjecting the sample to a variable external magnetic field;

means for measuring the magnetic field intensity of the magnetic field generated by said magnetic field generating means;

a signal sensor for measuring Barkhausen signals from the sample when the sample is subjected to the external magnetic field; and signal processing means responsive to the magnetic field intensity measured by the magnetic field intensity measuring means and the Barkhausen signals measured by the signal sensor for forming a jump sum rate first moment signal corresponding to a center of gravity of a jump sum rate of the Barkhausen signals with respect to the magnetic field intensity, and for determining the at least one mechanical or magnetic characteristic responsive to the jump sum rate first moment signal.

2. An apparatus according to claim 1, wherein said magnetic field generating means comprises an energizing yoke.

3. An apparatus according to claim 1, wherein said magnetic field intensity detecting means comprises a Hall probe.

4. An apparatus according to claim 1, wherein said signal sensor comprises a surface coil.

5. An apparatus according to claim 1, wherein said signal sensor comprises a sensor array.

6. An apparatus according to claim 1, wherein said at least one mechanical or magnetic characteristic of the sample is hardness.

7. An apparatus according to claim 1, wherein said at least one mechanical or magnetic characteristic of the sample is coercive field strength.

8. An apparatus according to claim 1, wherein said at least one mechanical or magnetic characteristic of the sample is yield strength.

9. An apparatus according to claim 1, wherein said at least one mechanical or magnetic characteristic of the sample is ultimate strength.

10. An apparatus according to claim 1, further comprising output means, coupled to said signal processing unit, for outputting information relating to the mechanical characteristic of the sample.

11. An apparatus according to claim 10, wherein said output means comprises a printer.

12. An apparatus according to claim 10, wherein said output means comprises a monitor.

13. An apparatus according to claim 1, wherein said signal processing unit establishes a threshold level for determining whether the Barkhausen signals measured by the signal sensor are deemed to be valid.

14. An apparatus according to claim 1, further comprising means for applying stress to said sample, when said magnetic field intensity and Barkhausen signals are measured.

15. An apparatus according to claim 1, further comprising means for measuring ordinary magnetic properties of said sample when said magnetic field intensity and Barkhausen signals are measured.

16. An apparatus according to claim 1, further comprising control means for receiving a signal representing said at least one mechanical or magnetic characteristic from said signal processing means and for controlling at least one parameter of a process performed using the sample.

17. An apparatus according to claim 16, wherein at least one of said signal processing means and said control means uses artificial intelligence for optimizing the control of said at least one parameter.

18. A method of measuring at least one mechanical or magnetic characteristic of a ferromagnetic sample as a function of at least one magnetic characteristic of the sample, the method comprising the steps of:

subjecting the sample to a variable external magnetic field;

measuring magnetic field intensity of the magnetic field to which the sample is subjected;

measuring Barkhausen signals from the sample when the sample is subjected to the external magnetic field; and forming a jump sum rate first moment signal corresponding to a center of gravity of the jump sum rate of the Barkhausen signals with respect to the measured magnetic field intensity responsive to the measured magnetic field intensity and the measured Barkhausen signals, and determining the at least one mechanical or magnetic characteristic responsive to the jump sum rate first moment signal.

19. A method according to claim 18, further comprising the step of providing a signal representative of said at least one mechanical or magnetic characteristic to a feedback control loop for controlling parameters of said method.

* * * * *